United States Patent
Todd et al.

(10) Patent No.: US 7,326,054 B2
(45) Date of Patent: Feb. 5, 2008

(54) METHOD AND APPARATUS FOR DRILLING TEETH WITH A PRESSURIZED WATER STREAM

(75) Inventors: Robert Todd, Provo, UT (US); Scott Hansen, Fairfax, VT (US)

(73) Assignee: Brigham Young University, Provo, UT (US)

( * ) Notice: Subject to any disclaimer, the term of this patent is extended or adjusted under 35 U.S.C. 154(b) by 155 days.

(21) Appl. No.: 10/344,835

(22) PCT Filed: Aug. 23, 2001

(86) PCT No.: PCT/US01/26364

§ 371 (c)(1),
(2), (4) Date: Feb. 13, 2003

(87) PCT Pub. No.: WO02/15810

PCT Pub. Date: Feb. 28, 2002

(65) Prior Publication Data

US 2003/0207232 A1    Nov. 6, 2003

(51) Int. Cl.
*A61C 3/02* (2006.01)
(52) U.S. Cl. .................................................. 433/88
(58) Field of Classification Search ............... 433/88, 433/80–82; 601/162–165
See application file for complete search history.

(56) References Cited

U.S. PATENT DOCUMENTS

| | | | |
|---|---|---|---|
| 3,863,628 A | 2/1975 | Vit | |
| 3,972,123 A * | 8/1976 | Black | ............. 433/88 |
| 4,012,842 A | 3/1977 | Vit | |
| 4,522,597 A | 6/1985 | Gallant | |
| 4,540,365 A * | 9/1985 | Nelson et al. | ............. 433/88 |
| 4,776,794 A | 10/1988 | Meller | |
| 5,092,744 A * | 3/1992 | Boers et al. | ............. 417/397 |
| 5,203,698 A | 4/1993 | Blake et al. | |
| 5,275,561 A | 1/1994 | Goldsmith | |
| 5,525,058 A | 6/1996 | Gallant et al. | |
| 5,601,430 A | 2/1997 | Kutsch et al. | |
| 5,741,247 A | 4/1998 | Rizoiu et al. | |
| 5,759,031 A | 6/1998 | Goldsmith et al. | |
| 5,785,521 A | 7/1998 | Rizoiu et al. | |
| 5,934,904 A | 8/1999 | Elrod et al. | |

(Continued)

FOREIGN PATENT DOCUMENTS

DE     19804065 A1     12/1999

(Continued)

OTHER PUBLICATIONS

Webpage, Biolase Technology, Inc., 1997-2000.

(Continued)

*Primary Examiner*—John J Wilson
(74) *Attorney, Agent, or Firm*—Madson & Austin (57) ABSTRACT

An apparatus and method are disclosed for boring into teeth to remove decaying tool matter using a high pressure jet of water. A system according to the invention may include a pressurized water source operably connected to an applicator used to target the water stream at the decayed portion of the tooth. The invention contemplates water streams utilizing single or multiple stream orifices, pure water or particle-entrained streams, and constant high pressure or pulsing pressure to accomplish removal of oral material, including enamel.

6 Claims, 7 Drawing Sheets

U.S. PATENT DOCUMENTS

| | | |
|---|---|---|
| 5,968,037 A | 10/1999 | Rizoiu et al. |
| 6,086,367 A | 7/2000 | Levy |
| 6,164,966 A | 12/2000 | Turdiu et al. |
| 6,224,378 B1 | 5/2001 | Valdes et al. |
| 6,231,567 B1 | 5/2001 | Rizoiu et al. |
| 6,254,597 B1 | 7/2001 | Rizoiu et al. |

FOREIGN PATENT DOCUMENTS

| | | |
|---|---|---|
| WO | WO-97/06924 | 2/1997 |

OTHER PUBLICATIONS

Ebisch, Robert, "Cavity's Rainbow, Taking the Dreaded Drill out of Modern Dentistry," Sky Magazine, Mar. 2001, pp. 96-97.

* cited by examiner

METHOD AND APPARATUS FOR DRILLING TEETH WITH A PRESSURIZED WATER STREAM

BACKGROUND OF THE INVENTION

1. Field of the Invention

The present invention relates to the field of drilling teeth to remove decayed enamel or other tooth matter and provide a surface of the proper size and shape to receive a dental restorative filling. More specifically, the present invention relates to a method and apparatus for drilling teeth with one or more high-pressure water streams with or without abrasive materials suspended in the water.

2. Technical Background

According to the American Dental Association survey center, in 1990 alone, there was an estimated 151,810,000 dental filling procedures performed in the United States. Currently the most widespread and notorious method for removing tooth matter in a cavity filling procedure is through a high speed drilling process. Drilling is often associated with substantial discomfort and anxiety. Most people find going to the dentist and having a cavity filled a very unpleasant and painful experience. Some people even develop phobias of visiting the dentist from the accompanying sounds, smells, and pains present in a typical drilling process.

A high speed dental drill is a mechanical drill that is driven by an electrical or pneumatic power source with a bit at the end. The drill bit is designed to remove small pieces of tooth as its rotating head contacts a tooth. This removal method functions much in the same manner as does an industrial drill when removing portions of metals or ceramics. A dental drill is typically handheld and easy to position in most areas of the mouth for removing tooth decay. The drilling process often requires water to cool the tooth being drilled and a vacuum to remove the water and tooth debris. The drilling process has the advantage of being low cost and well accepted in the dental field. Nonetheless, drilling does have many disadvantages in dental applications. cutting action of the rotating bit may damage the enamel, which may weaken the structure of the tooth. The process is intrusive for the patient and the size of the drill bit often requires the removal of considerable more healthy material than would otherwise be necessary.

The patient often experiences discomfort from the grinding and vibrations in the vicinity of tooth nerves that may already be stressed due to decay of enamel. During this process, the patient hears the constant, high-pitched whine of the drill motor, which is associated with pain and discomfort by many people, and may be downright frightening for others. To compensate for the pain and discomfort of a drilling procedure, large amounts of pain reducer may be required which can lengthen the process as a result of the necessity of waiting for the medicine to take effect. The use of medication also increases the cost of the procedure. The result of these problems is that the process of drilling a tooth entails several minutes, or even hours, of discomfort and anxiety for the patient.

Alternative methods of removing decaying tooth matter have been investigated to overcome the shortcomings of dental drilling. One such method is air abrasion. Air abrasion units use pressurized air to propel and direct small abrasive particles onto the tooth resulting in an abrading away of the surface. An abrasion units are used quite effectively for shallow, surface cavities and tend to conserve more of the healthy tooth than the high speed drill. Also, because the impact of the abrasive particles on the tooth are so minute, vibrations are insignificant and usually pain relief injections are not required. This saves time and also increases comfort to the patient. However, the air abrasion method is not as time effective when it comes to drilling below the outer enamel layer of the tooth and into softer tissues. This is due, in part, because the softer tissue just beneath the enamel surface, called dentin, partially absorbs the impact of the abrasive particles. The particles tend to bounce off this portion of the tooth, diminishing the excavating effects of the abrasive stream.

Another alternative to drilling that has been introduced recently is laser drilling and cutting technology. Lasers are the most precise method of removing tooth matter in the dental industry. They are capable of penetrating the tooth surface and underlying tissues in a highly controlled fashion and with the smallest width of cut of all of the presently available methods. Although the use of lasers does produce a heat-affected zone on areas of the tooth adjacent to the cut, several studies have shown that these effects are not significant enough to cause permanent damage to the health of the tooth. Although the laser offers significant benefit in dental applications, very few dentists use them. This is primarily due to the fact that they cost significantly more than alternative methods. Also, most dentists are not yet ready to invest in a technology without knowing that it provides significant improvements over their current method.

In developing a new decay removal method there is a need for an apparatus and method capable of removing decayed tooth material that is better suited to preserve a maximum amount of healthy tooth material. Leaving as much healthy tooth matter in place as possible helps to maintain the overall strength of the tooth and minimize the chances of cracking the tooth later on. In the case of the high speed drill, the minimum cutting dimension is limited by the width of the cutting tool. Relatively large amounts of healthy tooth material have to be removed in order to sufficiently reach the decayed portions. The air abrasion and laser methods have the ability to make smaller cuts and are thus able to conserve much more of the healthy tooth than had previously been possible. But, with the more precise cutting abilities also comes a limitation in the speed of the process, type of material that can be removed, and the cost of the equipment required. Because these methods are able to remove only relatively tiny sections of a tooth at a time, they also require more time to remove larger sections of material.

Consequently, there is a need for an improved apparatus and method for drilling teeth. The method should be effective for rapidly removing enamel and other decayed material with a minimum of discomfort for the patient. Thus, the apparatus should preferably operate quietly and with a minimum of appliance that must be simultaneously inserted into the patient's mouth. Furthermore, the apparatus should operate inexpensively, and function with equipment easily integrated with current dental office systems. Such a device should be self-cooling and accurate, so that healthy tooth structure is preserved. Moreover, such a method should minimize pain to the patient and should not be psychologically stressful for the patient, for whom the prospect of going to the dentist is already distressing enough.

SUMMARY OF THE INVENTION

The present method and apparatus implements high pressure liquid forced through a small orifice, or water jet, to cut and remove decaying tooth matter for restorative dental procedures. Water jets are able to cut through many materials much easier than other methods without harming the surrounding material. The present apparatus includes a pressure source configured to provide a flow of pressurized liquid, such as water, to an applicator through a high pressure conduit. The applicator has a first orifice positioned to direct a first stream of the liquid against an oral surface, wherein the velocity of the stream of liquid ejected from the orifice is capable of boring into tooth matter, such as tooth enamel.

The water jet dental tool may also have an abrasive material suspended within the pressurized liquid. The abrasive is typically mixed with a liquid to make a generally homogenized slurry. The abrasive material in the slurry may be sized from 1 to 30 microns in diameter and has a volumetric concentration of abrasive in the range of 3% to 20%. Any number of abrasive materials may be used in the present apparatus and method. Aluminum oxide, pumice, baking soda, and illminite are abrasives that are presently used in the dental field and are also capable of removing a sufficient amount of tooth and oral matter when used in a water jet system. The slurry is ejected out of the applicator under high pressure. Typically slurry pressures may range from 250 psi to 17,000 psi and more preferably, from 500 psi to 2,500 psi. Other embodiment may have useful slurry pressures below 250 psi, depending on other factors, such as the slurry and orifice size.

The orifice in the applicator may have various shapes for different boring requirements. The orifices in one embodiment are circular, and in another embodiment the orifices are elliptical. However, other shapes of orifices may be implemented in the water jet for a large range of dental applications. The orifice size may be of a range of 0.003 inches (0.076 mm) to 0.008 inches (0.203 mm). Additionally, the applicator may have more than one orifice to direct a stream of water at a tooth and may further be able to induce cyclical variations in the liquid pressure.

The present method may also be practiced through other apparatuses by embodying the present procedure. The process comprises pressurizing a liquid. The pressure can be of any number of ranges depending upon slurry composition. The pressurized liquid is then conveyed into an applicator. The applicator can have any number of orifices of a diameter sufficient to bore into teeth. The applicator then ejects a stream of high pressure liquid or slurry from an orifice with a velocity sufficient to bore into a tooth.

The operation, features, and advantages of the present apparatus and method will become more fully apparent from the following description and appended claims, or may be learned by the practice of the invention as set forth hereinafter.

DETAILED DESCRIPTION

The presently preferred embodiments of the present invention will be best understood by reference to the drawings, wherein like parts are designated by like numerals throughout. It will be readily understood that the components of the present invention, as generally described and illustrated in the figures herein, may be arranged and designed in a wide variety of different configurations. Thus, the following more detailed description of the embodiments of the apparatus, system, and method of the present invention, as represented in FIGS. 1 through 8, is not intended to limit the scope of the invention, as claimed, but is merely representative of presently preferred embodiments of the invention.

Figure 1:
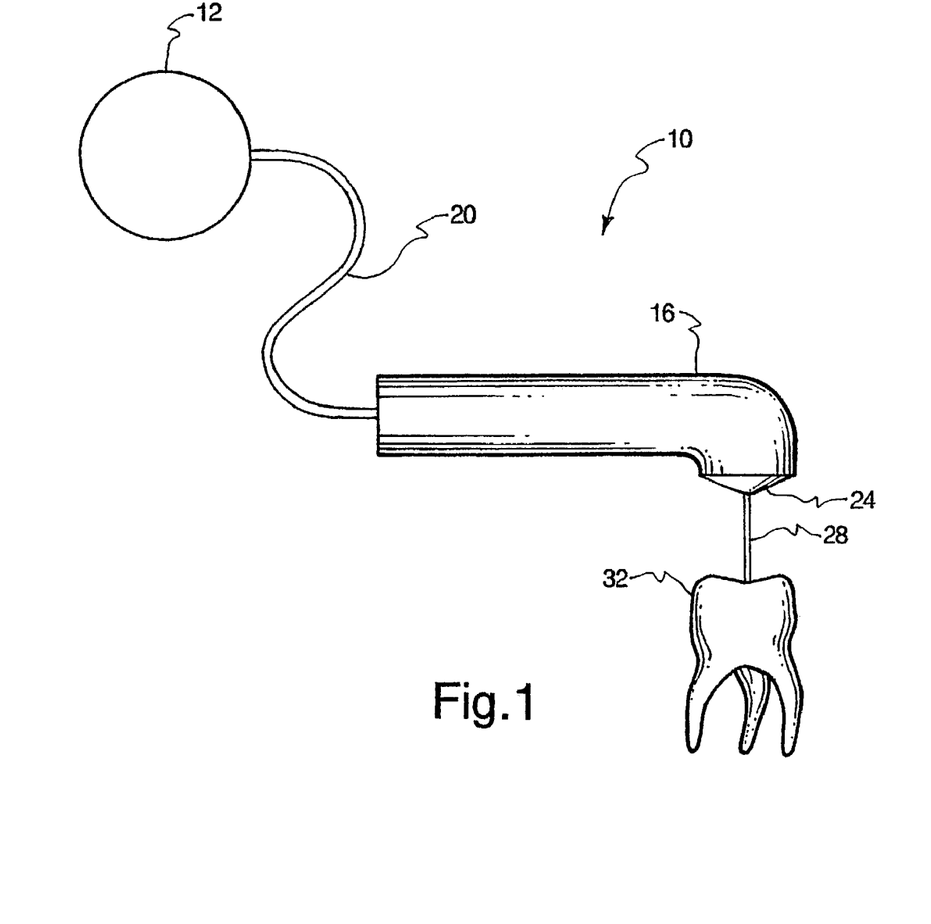
FIG. 1 is a schematic block diagram of a water jet dental tool.

Referring to FIG. 1, a water jet dental tool 10 is depicted as having a pressurized liquid source 12 and a liquid stream applicator 16. The pressurized liquid source 12 and the applicator 16 are operably connected, such that the applicator 16 receives a high pressure liquid from the pressure source 12. The pressurized liquid source may be a high pressure liquid pump or other pressure creation device, such as a pressurized tank of gas, a weighted piston, or a compressed flexible bladder. The pressurized liquid source 12 and the applicator 16 may be connected by any liquid transferring device capable of withstanding high pressures. High pressure hosing, drilled sections of block, or any other like high pressure conduits 20 may be employed in the present system 10. Once the high pressure liquid reaches the applicator 16, it is ejected from the water jet 10 through an orifice 24, having a diameter that is smaller than the diameter of the high pressure conduit 20.

The constant volumetric flow rate of such a nozzle system converts the high pressure liquid into a high velocity liquid as it passes though the orifice. The fine stream of liquid 28 is directed by the applicator 16 at the desired oral matter, such as a tooth 32, as depicted in FIG. 1. The high velocity liquid stream 28 impacts the surface of the tooth, causing the water to decelerate. The deceleration of the liquid stream 28 produces a reaction force in the tooth 32 in a direction toward the tooth 32 and in the same direction of the liquid stream 28. Because a force equals a mass multiplied by an acceleration, the deceleration of the liquid multiplied by the mass of the liquid impacting the tooth 32 produces a force on the tooth 32 sufficient to remove tooth matter. FIG. 1 depicts a possible tooth decay removal procedure. However, this water jet dental tool 10 is also capable of removing healthy tooth matter, such as in smoothing out chips, or removing soft oral matter, such as in a root canal procedure. A water jet dental tool 10 can be used in many of the same applications as a conventional drill.

Various embodiments of the dental tool depicted in FIG. 1 exist. For example, FIG. 2 demonstrates a water jet wherein the liquid is combined with an abrasive to create an abrasive slurry. A slurry is a mixture of a liquid, often water, and any of several finely divided particle substances. The slurry travels though the water jet system in the same manner as a liquid, but it additionally provides an abrasive to facilitate removal of tooth matter or other similar substances. In an oral environment, the particles selected to mix with the liquid must be selected with consideration of applicable health standards. Abrasive materials, such as aluminum oxide, that are already used in dental applications are preferable because the material has already been approved by the United State Food and Drug Administration for dental applications. Other abrasive materials such as pumice, baking soda, and illminite are also safe in oral environments and can be used in tooth matter removal. In addition to being safe, the abrasives must also have other important physical properties, such as particle size, volumetric concentration, hardness, and insolubility.

Particle size of the slurry abrasive material is a factor in determining and controlling the amount of material removed by the liquid stream. In one embodiment for removing decaying tooth matter, the abrasive particle size is preferably in the range of 1 to 30 microns. The particle size is typically classified based on the size of screen or filter through which the material passes. Reference in this section or in other sections to particle size should be not be construed to limit an abrasive to any one particle size. For example, a quantity of 20 micron aluminum oxide may include a certain percentage of particles that are larger or smaller than 20 microns, as typically occurs in a screening process. Rather, a quantity of 20 micron aluminum oxide will be made substantially, not entirely, of 20 micron particles. Further, other materials may be present in a slurry besides a liquid and abrasive particles. For example, various types of pain reducers or cleaning materials may be within the slurry to provide a wide variety of applications and types of slurry. Also, various materials to aid in suspending the abrasive particle in the slurry may be used.

In a preferred embodiment, the liquid in the slurry has a 4% to 17% volumetric concentration of abrasive. This preferred range allows for the slurry to generally remain a liquid, while also containing an adequate amount of abrasive for cutting. A correct ratio of abrasive to liquid allows for optimal functions of a water jet. The slurry should remain substantially liquid to allow for pressurization of the liquid in a pump, pressure intensifier, or other pressure source. However it is also desirable, for safety and power generation reasons, to have the system operate at a low range of pressures.

While the volumetric concentration range of 4% to 17% is preferred for one embodiment, other ranges are within the scope of this disclosure. For example, the present apparatus is capable of removing oral matter without the use of an abrasive. This may be used in situations with highly decayed tooth or with treatment of gums. Higher concentrations of abrasives may also be used with this water jet system, but attention must be paid to prevent the slurry from becoming a sludge. Additionally, higher concentrations of abrasive can create a messy residue around the work area. A volumetric concentration of 17% provides a good mixture for efficient cutting, but it leaves a residue of spray around the work area from abrasive particles. A mixture at 11% volumetric concentration is substantially cleaner than a higher concentration of abrasive, but does not cut as effectively as with 17% abrasive. Thus, the particular environment and application should be considered when selecting a volumetric concentration of abrasive in the pressurized liquid.

Presently, water is a preferred liquid for the slurry because of its safety and availability. However, other liquids may be used so long as they are able to create a pressure and are able to suspend an abrasive. Such liquids may have some desirable traits that are absent in water. Water is an excellent solvent, which limits the number of types of abrasives that can be used in water jet. For example, baking soda can be used in a water jet application, but it dissolves in the water, thus limiting its abrasive features. Additionally, it can be difficult to keep such an abrasive homogenous throughout the system. Keeping a slurry homogenous is helpful in calibrating and timing the duration for exposing the tooth to a high pressure stream of slurry. A liquid, other than water, in which abrasives have lower solubility may be used in the water jet.

Referring back to FIG. 2, this embodiment depicts a system having two possible devices and locations for mixing a slurry in a water jet dental tool 40. The system has a pump or other pressure source 44 that receives a liquid from a liquid source 48. An abrasive mixer 50, 52 may be located on either side of the pump. The system need not have both mixers 50, 52, but will typically have one or the other. The mixer 50 on the upstream side of pump 44, receives a measure of abrasive from the abrasive feeder 56 based upon the volume of liquid flowing through the system. The upstream mixer 50 receives both the liquid and the abrasive to combine them to create a slurry of proper concentrations. The slurry then enters the pump where it is pressurized to a high pressure. Once the slurry is pressurized, it flows through the high pressure conduit 60. The slurry enters the applicator 64 where it is directed at the material to be cut. However, there are some drawbacks to this embodiment. The slurry being pressurized in the pump can cause significant wear of the pump components, causing the pump to leak or fail.

Figure 2:
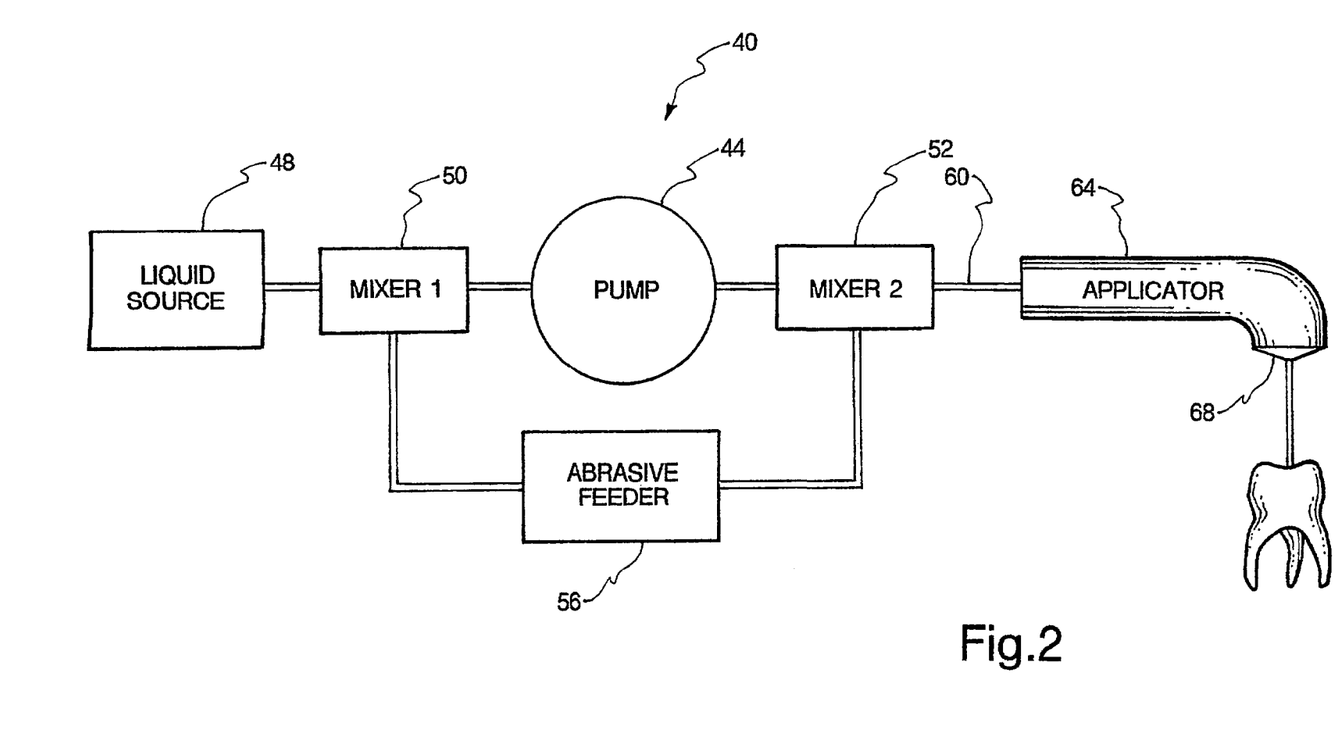
FIG. 2 is a schematic block diagram of another possible embodiment of a water jet dental tool, with abrasive mixers.

To avoid this damage, the abrasive may be added to the pressurized liquid by a downstream mixer 52. For this abrasive mixing process, the abrasive should be either in a single batch form or should be injected intermittently as a slurry into the pressurized liquid at a higher differential pressure stream. For a single batch injection procedure, the batch is generally fed into the system in quantities suited for limited boring time and depth. But, because dental restorative work typically only involves a few dental boring procedures per visit, the downstream mixer configuration is well suited for dental procedures. Alternatively, lower pressure embodiments may be able to adequately add an abrasive downstream of the pressure source without any additional modifications or operations. In a further embodiment, the system may not mix an abrasive with a liquid at all, but may simply rely upon an abrasive free liquid for the cutting functions.

The advantages and disadvantages of each abrasive injection method must be considered in selecting a design for an application. Presently, locating the mixer 52 downstream of the pump or other pressure source is preferred to maintain the life of the pump or pressure source. A batch of abrasive may be loaded into the abrasive feeder to provide a fixed amount of abrasive for multiple oral procedures. However, a pump capable of pressurizing a slurry with minimal wear to the system would be preferable.

Figure 3:
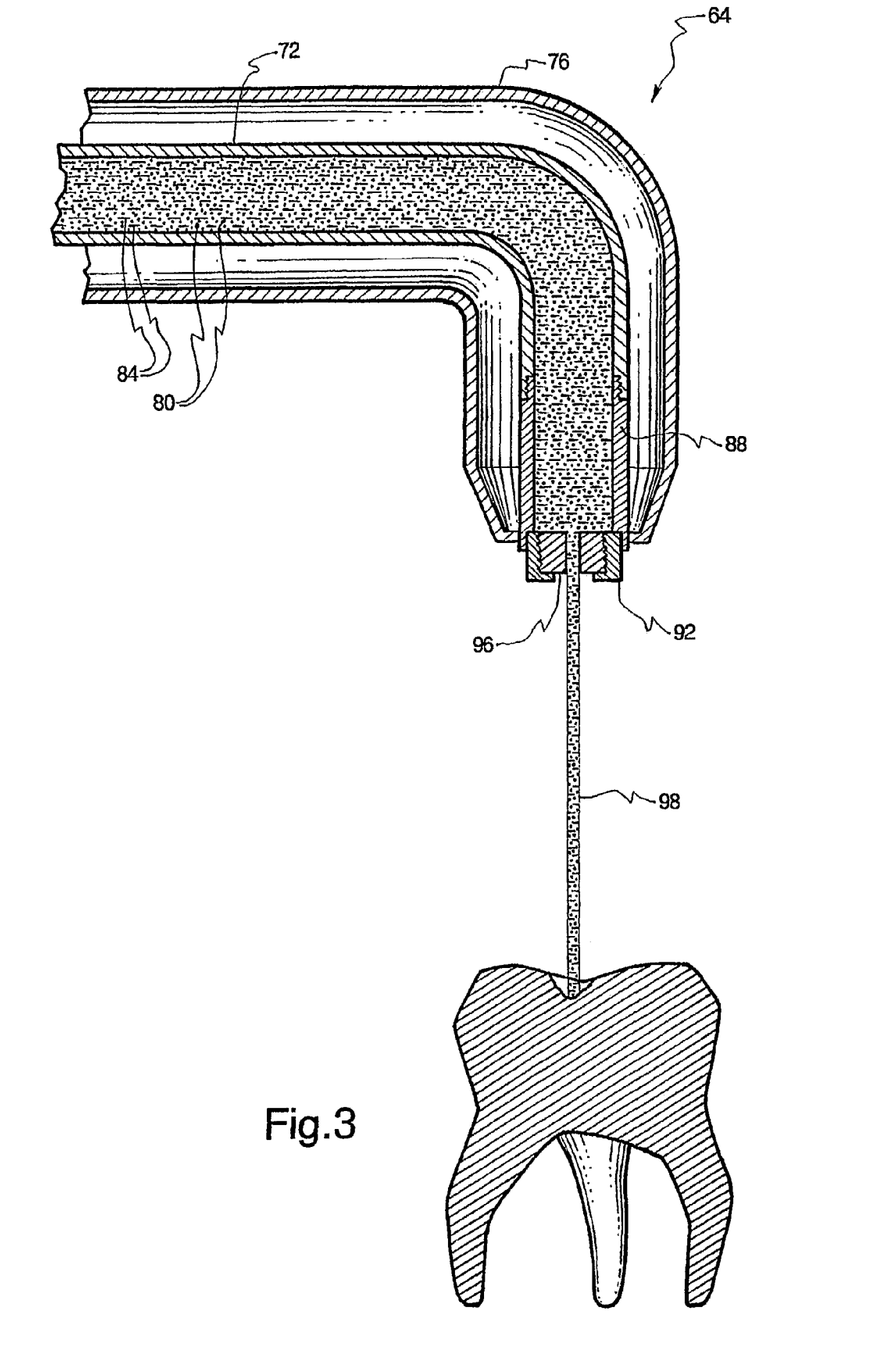
FIG. 3 is a cross-sectional view of a slurry applicator.

Regardless of where the slurry is mixed, the mixture enters into the applicator 64 as a slurry and exits the orifice 68. FIG. 3 depicts a cross-sectional view of the applicator 64 of FIG. 2. A tube or channel 72 is present in the body 76 of the applicator and is capable of sustaining a high pressure, such as is present in a water jet system. The channel 72 is shown as having a slurry running through it, as is represented by the particles 80 in the liquid 84. The slurry mixture travels through the channel 72 and into nozzle 88 coupled to the end of the channel 72. The nozzle 88 has a collet 92 that supports an orifice 96. The slurry is forced through the small orifice 96 by the internal pressure of the mixture. The dynamics of the relationship of pressure to velocity of the slurry can be best related by Bernoulli's equation. Bernoulli's equation relates liquid pressure, velocity, density, and elevation for two points in a fluid system with a constant flow rate. In the water jet, the volume of the liquid entering the system is equal to the volume of water exiting the orifice 96, because there are no other liquid inputs and output sources. For this reason Bernoulli's equation is appropriate for water jet calculations. In the equations below, the first measurement is taken at a pressurized point in the system and the second measurement is taken just after the liquid exits the orifice. The equation states:

$$\frac{P_1}{\rho} + \frac{V_1^2}{2} + gz_1 = \frac{P_2}{\rho} + \frac{V_2^2}{2} + gz_2$$

Wherein:
$P_1$=Pressure of liquid inside the system;
$P_2$=Pressure of liquid exiting the orifice;
$V_1$=Velocity of liquid inside the system;
$V_2$=Velocity of liquid exiting the orifice;
$\rho$=The density of the liquid;
g=Gravity;
$z_1$=Elevation of liquid inside the system; and
$z_2$=Elevation of liquid exiting the orifice.

This equation allows for a water jet system to be characterized according to the various design parameters. The significant factors in dental water jet applications are the exit velocity of the liquid stream, applicator distance from the tooth, the internal pressure of the liquid, size of the stream, and the density of the liquid. For example, if an exit velocity is known, then the above equations may be used to solve for the internal pressure required to obtain the known exit velocity. This may be useful where a dentist understands the relationship between the cutting velocity to the cutting depth of the slurry stream. However, to simplify in calculating the pressure, several assumptions can and should be made. First, there is an assumption of minimal frictional losses as the liquid travels through the system. While, frictional losses do occur, neglecting these losses presents only a small degree of inaccuracy while greatly simplify the calculations. Second, the pressure as the liquid exits the nozzle is assumed to be at atmospheric pressure (about 14.7 psi). Pressures at the exit location of the liquid may actually vary slightly, but not significantly. Third, the elevation change between the first point and the second point are assumed to be minimal when compared to the pressures difference of the two pressures. And finally, the first velocity in the water may be assumed to be zero when compared to the exit velocity at the second point. If these assumptions are followed and the equation is solved for the internal pressure of the water:

$$P_2 = \frac{\rho V_2^2}{2} + P_1$$

The equation states that to obtain a velocity of 100 inches per second to 1000 inches per second the pressure in the system should be approximately 200 psi to 18,000 psi respectively. Thus, the exit velocity can be scaled to an associated pressure for calibration purposes. In the embodiment depicted in FIG. 2 and FIG. 3, the preferred operational pressures are between 250 psi and 17,000 psi. The optimum pressure ranges may vary depending on the preferred abrasive type, volumetric concentration, orifice size, liquid type, and other factors. Other pressure ranges may be preferable when different values and materials are used. For example, the present system may operate at a generally low pressure for specific applications wherein the abrasive has larger sizes and higher concentration. Such an embodiment would be covered within the scope of the present water jet dental tool.

While the pressure range of 250 psi to 17,000 psi is preferred for the present system, the water jet is most practically operated at a range of 500 psi to 2,500 with the currently preferred slurry characteristics, the presently preferred slurry being an 20 micro aluminum oxide/water slurry having a volumetric concentration of 11% This pressure range provides for controlled boring of a tooth, low-cost equipment, and safer operation. As is intuitive, the higher the liquid pressure, the faster the stream will bore a hole in the tooth. Thus to allow for optimal control of a boring procedure, a lower pressure should be maintained. Use of a lower pressure, will require less expensive equipment. The cost of high pressure pumps, valves, and hosing may limit the cost feasibility of a water jet dental tool, low pressure operation may allow the machine to remain affordable. Further, low pressure ranges are safer than higher pressure ranges because less energy is stored in the liquid. An alternative embodiment may implement both high and low pressures during a single procedure. The system may be configured to oscillate the pressure of the fluid, which in turn oscillates the velocity of the fluid exiting the orifice. The oscillating device may be a pump capable of producing pressure spikes in the fluid, or a valve that cuts the fluid flow at various intervals.

Figure 4:
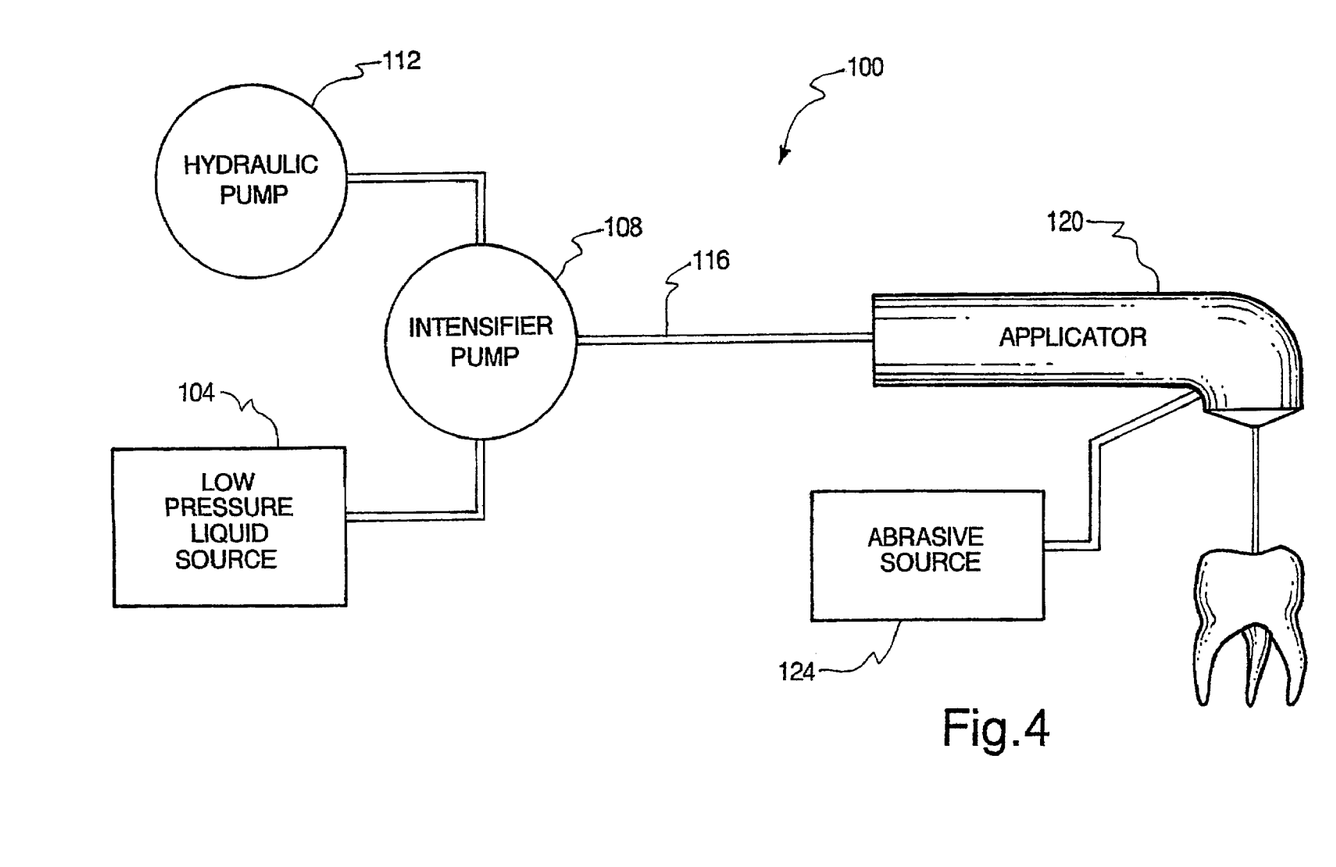
FIG. 4 is a schematic block diagram of another possible embodiment of a water jet dental tool, with an abrasive source and an intensifier pump.

Returning to back to the figures, FIG. 4 depicts an alternative embodiment of a water jet system having a post-ejection abrasive mixer. Similar to the system of FIG. 2, the water jet has a low pressure liquid source 104 that feeds the liquid into an intensifier pump 108 that pressurizes the liquid. A typical intensifier pump 108 may comprise of two cylinders aligned end-to-end, one cylinder large and one cylinder small. The pump 108 uses the simple principle of pressure equals force divided by area. As the area decreases the resulting force increases. Thus, as a large piston forces a liquid into the small cylinder, the pressure increases proportional to the difference between the two cylinder areas. While the pressure does increase, the system sacrifices flow rate of the liquid. However, because water jets require low flow rates, an intensifier pump is well suited for a water jet dental tool. The piston in the intensifier pump 108 may be driven by a hydraulic 112 or pneumatic pump, which in turn pressurizes the liquid. Once the liquid is pressurized, it travels through a high pressure conduit 116 and is directed though the applicator 120. The applicator 120 receives an abrasive from an abrasive source 124. The abrasive is mixed with the liquid in the applicator and the resulting slurry is ejected toward a tooth or other oral matter.

The applicator 120 in the present water jet dental tool may be handheld, similar to a dental drill type device. This allows for flexibility of use of the tool in a manner that a dentist would be familiar. Alternatively, the applicator may be attached to a positioning device placed in a location over the patient's mouth and the water jet stream may be set in different operating locations by a flexible arm or other positioning device. In another embodiment, the jet may be placed above the patient at a fixed position and the patient's head may be adjusted to receive a stream at the desired tooth location. In another embodiment, the location that the liquid stream will impact a tooth can be calibrated to aid the dentist in positioning the applicator 120. The applicator 120 may be equipped with a stylus to indicate the stream impact location. Alternatively, the applicator may have a light or a laser that indicates the bore location. Other embodiments of the present applicator 120 may exist that are consistent with the purpose and function of the present disclosure.

Figure 5:
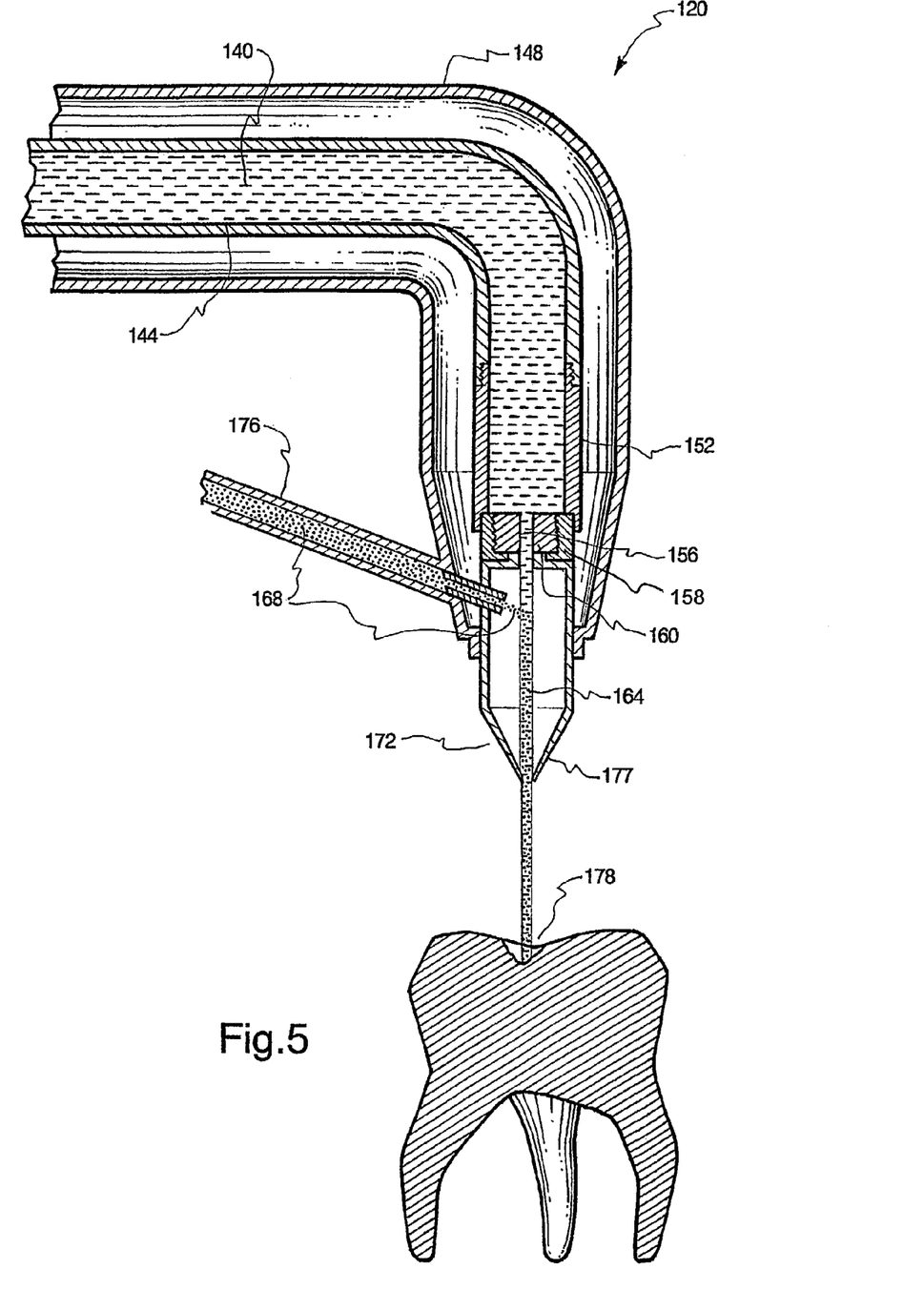
FIG. 5 is a cross-sectional view of an applicator having a post-ejection abrasive mixer.

FIG. 5 depicts a cross-section of the applicator having a post-ejection abrasive mixer. As with similar applicators, the liquid 140 travels through the channel 144 of the applicator 120. The channel 144 is fixed within the body 148 of the applicator and is shown within FIG. 5 as being a hose type conduit. The liquid 140 does not have any abrasive suspended within as it enters the nozzle 152. The nozzle in FIG. 5 is generally the same as the nozzle 64 in FIG. 3. The liquid enters the nozzle 152 and is forced out the orifice 156 in the orifice disk 160 at high speeds. At the point of ejection, no abrasives are present in the stream 164. In the embodiment of FIG. 5, the abrasive 168 is mixed with the high pressure stream 164 in a refocusing nozzle 172 after it leaves the orifice 156. The abrasive 168 is drawn through an abrasive feeding tube 176 and into the refocusing nozzle 172 by a vacuum created by the exiting liquid stream. Once the abrasive enters the refocusing nozzle 172, it is mixed with the liquid steam 164 to form a slurry. The liquid steam 164 is once again refocused into a fine stream by the tapered section of refocusing nozzle and ejected to the working area 178.

Figure 6:
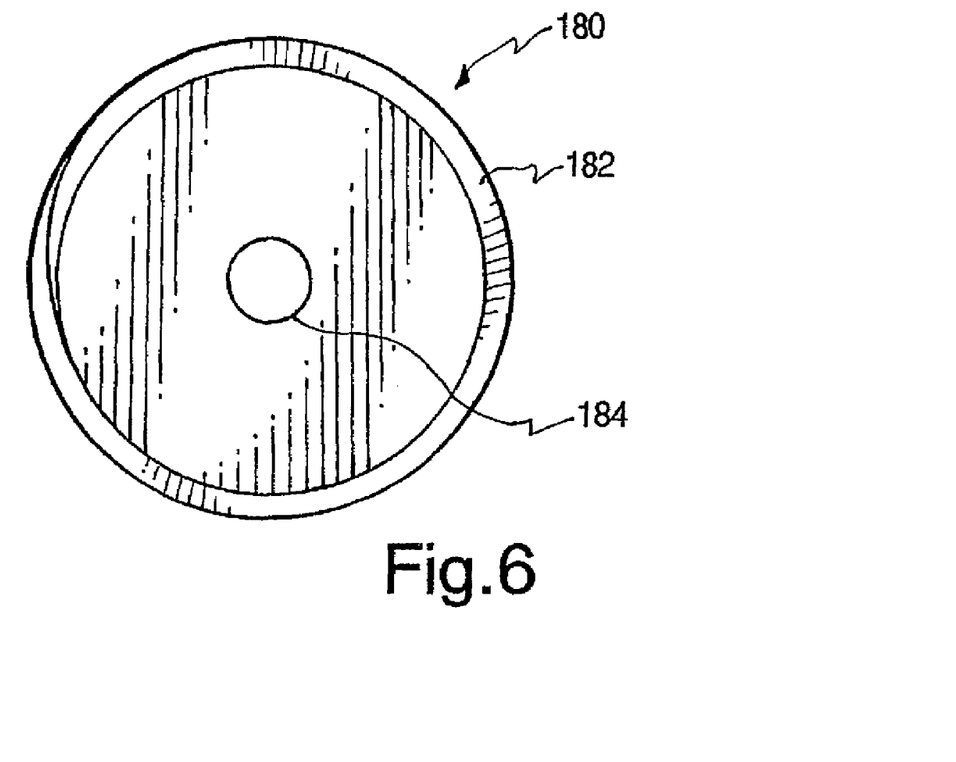
FIG. 6 is an end view of a liquid slurry orifice disk with a round orifice.
Figure 7:
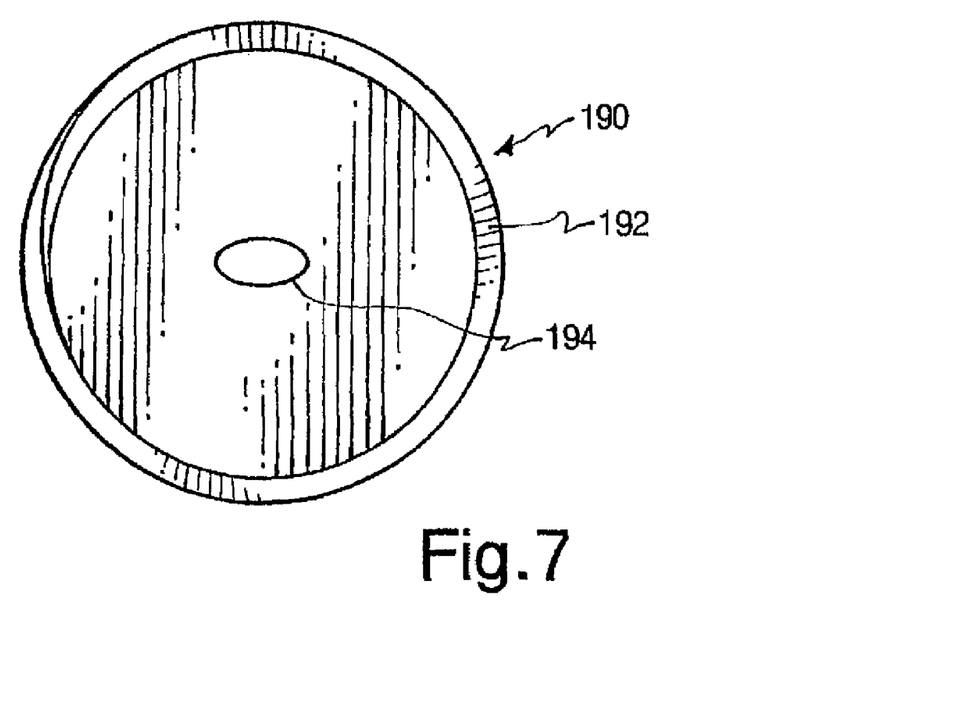
FIG. 7 is an end view of a liquid slurry orifice disk with an elliptical orifice.

The water jet removal tool, as depicted in FIG. 3 and FIG. 5, has a collet 92, 158 supporting an orifice disk 96, 160 respectively from which the slurry is ejected. FIG. 6 is a view of an orifice disk 180 held within a collet 182 have a round orifice 184. The round orifice 184 allows for a focused stream of slurry on a point of a tooth. The collet may have a threaded portion to be removably attached to a nozzle so that the orifice disk may be easily replaced without replacing the entire collet and nozzle assembly. FIG. 7 depicts an alternative embodiment of an orifice disk 190 having an elliptical orifice 194. The elliptical orifice 194 allows for removal of a rectangular area of decayed tooth or other oral matter. This shaped orifice provides the ability to create wide and shallow bores in a tooth. However, other shapes of orifices may be implemented in the water jet for a large range of dental applications. Additionally, the orifice in the orifice disk may further have a tapered exit wherein the stream diameter spreads out as it exits the orifice. Various degrees of taper can be used to obtain multiple stream and spray characteristics.

These orifice disks 180, 190 are typically made of a material that is not easily worn down by the abrasives, such as sapphire or diamond. The orifice size and shape is also an important design element of the water jet dental tool. The size of the exit orifice determines the amount of slurry ejected and the diameter of the cut in the tooth. A preferred embodiment is sized in the range of 0.003 inches (0.076 mm) to 0.008 inches (0.203 mm). However, other sizes for various applications will be known to one ordinarily skilled in the art. The small orifice also has a throttling effect on the liquid as it exits the nozzle. A throttling effect occurs as the size of the orifice is changed during a constant flow process according to the equations:

$$V_1 A_1 = V_2 A_2$$

Wherein:
$V_1$ = Velocity of liquid inside the system;
$V_2$ = Velocity of liquid exiting the orifice;
$A_1$ = Cross-sectional area of the tube;
$A_2$ = Cross-sectional area of the orifice;

While this equation demonstrates that the liquid will have a higher velocity as it exits the orifice, the effects of the throttling are generally nominal compared to the large pressure in the system. However, the throttle effect may have a noticeable effect on water jet systems when the pressures are lower.

Figure 8:
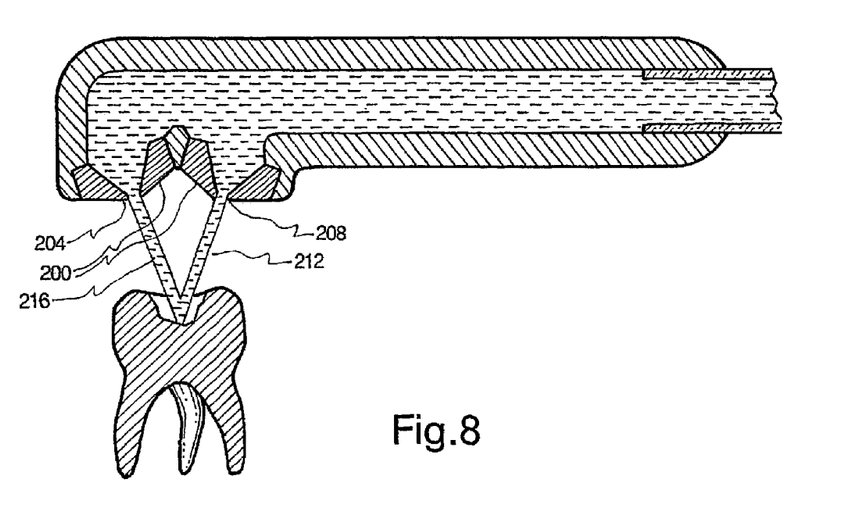
FIG. 8 is a cross-sectional view of a possible embodiment of an applicator, with a first and second orifice.

FIG. 8 depicts an orifice disk 200 having a first orifice 204 and a second orifice 208. The orifices 204, 208 can be slightly angled so that the two streams 212, 216 merge at one location on the tooth to increase the speed tooth matter is removed or to change the shape of the bore. Other embodiments may have more than two orifices depending upon the application.

The present water jet dental tool has a plurality of applications and variations that may be practiced as part of this disclosure. The method disclosed for removing tooth material using a water jet may perform many of the following steps, but may include alternative parameter ranges. First, a liquid is pressurized. A typical pressure is from 250 psi to 17,000 psi, but preferably from 500 psi to 2,500 psi. The pressurized liquid is then conveyed to an applicator and ejected out an orifice at a velocity sufficient to bore a hole in a tooth. The orifice may be of the range of 0.003 inches (0.076 mm) to 0.008 inches (0.203 mm). The method may also include a step of mixing an abrasive in the liquid so that abrasive is suspended in a slurry. One currently preferred abrasive is a slurry with a 4% to 20% volumetric concentration of abrasive aluminum oxide. The abrasive may have a size in the range from 4 to 27 microns.

The present invention may be embodied in other specific forms without departing from its structures, methods, or other essential characteristics as broadly described herein and claimed hereinafter. The present apparatus and system may be used in other applications as would be known to one skilled in the art, such as bone and finger nail etching. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

What is claimed is:

1. A method for drilling tooth matter comprising:
pressurizing a slurry to a pressure of about 250 psi to less than 500 psi, the slurry comprising a 3% to 20% volumetric concentration of aluminum oxide particles, wherein the aluminum oxide particles having an average particle size from 1 to 30 micron in diameter; and
jetting the pressurized slurry at tooth matter through a round orifice that is 0.004 inches (0.102 mm) to 0.006 inches (0.152 mm) in diameter, wherein the slurry bores into the tooth enamel when used on a patient.

2. The method, as recited in claim 1, wherein the aluminum oxide particles are mixed substantially homogenous throughout the pressurized slurry.

3. The method, as recited in claim 1, further comprising a second orifice.

4. The apparatus, as recited in claim 3, wherein the second orifice is disposed at an angle to the round orifice.

5. The apparatus, as recited in claim 3, wherein the second orifice is selectively disposed to direct a second stream of the pressurized slurry so that the stream from the second orifice merges with a stream from the round orifice at one location.

6. The apparatus, as recited in claim 1, wherein the pressurized slurry jetted via pulsed variations.

* * * * *

UNITED STATES PATENT AND TRADEMARK OFFICE
CERTIFICATE OF CORRECTION

| | |
|---|---|
| PATENT NO. | : 7,326,054 B2 |
| APPLICATION NO. | : 10/344835 |
| DATED | : February 5, 2008 |
| INVENTOR(S) | : Robert H. Todd et al. |

It is certified that error appears in the above-identified patent and that said Letters Patent is hereby corrected as shown below:

In column 1, line 65, please replace "surface. An abrasion units are used quite effectively" with --surface. Air abrasion units are used quite effectively--.

Signed and Sealed this

Twenty-seventh Day of May, 2008

JON W. DUDAS
*Director of the United States Patent and Trademark Office*